US012576049B1

(12) United States Patent
Orr et al.

(10) Patent No.: US 12,576,049 B1
(45) Date of Patent: *Mar. 17, 2026

(54) ONYCHOMYCOSIS TREATMENT METHODS

(71) Applicant: Hallux Inc., Laguna Hills, CA (US)

(72) Inventors: Robert L. Orr, San Clemente, CA (US); Christopher Ronald Agee, Lake Forest, CA (US); Thomas Mark Tremblay, San Francisco, CA (US)

(73) Assignee: HALLUX INC., Laguna Hills, CA (US)

( * ) Notice: Subject to any disclaimer, the term of this patent is extended or adjusted under 35 U.S.C. 154(b) by 943 days.

This patent is subject to a terminal disclaimer.

(21) Appl. No.: 17/712,742

(22) Filed: Apr. 4, 2022

Related U.S. Application Data

(63) Continuation-in-part of application No. 17/474,656, filed on Sep. 14, 2021, now Pat. No. 11,400,061, which is a continuation of application No. PCT/US2020/054710, filed on Oct. 8, 2020.

(60) Provisional application No. 63/171,457, filed on Apr. 6, 2021, provisional application No. 62/912,494, filed on Oct. 8, 2019.

(51) Int. Cl.
| | |
|---|---|
| *A61K 31/137* | (2006.01) |
| *A61K 9/00* | (2006.01) |
| *A61K 47/10* | (2017.01) |
| *A61K 47/14* | (2017.01) |
| *A61K 47/38* | (2006.01) |

(52) U.S. Cl.
CPC .......... *A61K 31/137* (2013.01); *A61K 9/0014* (2013.01); *A61K 47/10* (2013.01); *A61K 47/14* (2013.01); *A61K 47/38* (2013.01)

(58) Field of Classification Search
CPC ................................................. A61K 31/137
See application file for complete search history.

(56) References Cited

U.S. PATENT DOCUMENTS

| | | | |
|---|---|---|---|
| 9,446,009 B2 | 9/2016 | Kochinke et al. | |
| 9,931,282 B2 | 4/2018 | Restrepo et al. | |
| 2004/0062733 A1 | 4/2004 | Birnbaum | |
| 2005/0080075 A1* | 4/2005 | Nichols | A61P 35/00 544/44 |
| 2005/0186161 A1 | 8/2005 | Kawase et al. | |
| 2006/0165747 A1 | 7/2006 | Rolf | |
| 2007/0014743 A1 | 1/2007 | Birnbaum | |
| 2007/0196325 A1 | 8/2007 | Zhang et al. | |
| 2010/0048724 A1 | 2/2010 | Birnbaum et al. | |
| 2013/0210925 A1 | 8/2013 | Birnbaum et al. | |
| 2014/0276477 A1* | 9/2014 | Birnbaum | A61K 31/07 604/290 |
| 2014/0322293 A1 | 10/2014 | Kochinke et al. | |
| 2015/0111971 A1* | 4/2015 | Evers | A61P 31/02 514/655 |
| 2015/0342871 A1 | 12/2015 | Buyuktimkin et al. | |
| 2018/0311163 A1 | 11/2018 | Thuresson et al. | |
| 2019/0022000 A1 | 1/2019 | Tamarkin et al. | |

FOREIGN PATENT DOCUMENTS

| | | |
|---|---|---|
| CA | 2783891 A1 | 6/2011 |
| WO | 2006013963 A1 | 2/2006 |
| WO | 2008036595 A2 | 3/2008 |
| WO | 2011155640 A1 | 12/2011 |
| WO | 2017163091 A1 | 9/2017 |

OTHER PUBLICATIONS

Alio, Md et al., "Dermatophytes growth curve and in vitro susceptibility test: a broth micro-titration method," Medical Mycology, Jun. 2005; 43(4):319-325.
Bhatt et al., "Efinaconazole Topical Solution, 10%: Formulation Development Program of a New Topical Treatment of Toenail Onychomycosis," Journal of Pharmaceutical Sciences, 2015; 104:2177-2182.
Bristow et al., "Rapid Treatment of Subungual Onychomycosis Using Controlled Micro Nail Penetration and Terbinafine Solution," Journal of Drugs in Dermatology, Aug. 2016; 15(8):974-978.
Canavan et al., "Subungual Space: The Next Frontier," Skin Appendage Disorders, 2019; 5:50-51.
Dolton et al., "Terbinafine in Combination with Other Antifungal Agents for Treatment of Resistant or Refractory Mycoses: Investigating Optimal Dosing Regimens Using a Physiologically Based Pharmacokinetic Model," Antimicrob. Agents Chemother., 2014; 58(1):48-54.
Elewski et al., "Access of Efinaconazole Topical Solution, 10%, to the Infection Site by Spreading Through the Subungual Space," Journal of Drugs in Dermatology, Nov. 2014; 13(11):1394-1398.
Elewski, Md, "Study Evaluating the Effect of Jublia on Dermatophytomas," NIH—U.S. National Library of Medicine, 2018; 10 pgs. Retrieved from: https://clinicaltrials.gov/ct2/show/NCT03098615?cond=onychomycosis&draw=13&rank=100.
Geyer et al., "Modulation of linear nail growth to treat diseases of the nail," J Am Acad Dermatol., Feb. 2004, 50:229-34.
Ghannoum et al., "Fungal Nail Infections (Onychomycosis): A Never-Ending Story?" PLOS Pathog, Jun. 2014; 10(6):e1004105; 6 pgs. https://doi.org/10.1371/journal.ppat.1004105.
Goodfield et al., "Combined treatment with surgery and short duration oral antifungal therapy in patients with limited dermatophyte toenail infection," J Dermatol Treat, 2000; 11:259-262.

(Continued)

*Primary Examiner* — Genevieve S Alley
(74) *Attorney, Agent, or Firm* — Umberg Zipser LLP

(57) ABSTRACT

A method for treating onychomycosis uses a treatment protocol that atraumatically and subungually administers an antifungal agent dissolved in a liquid pharmaceutical composition to a subungual space to so achieve a minimum inhibitory concentration of the antifungal agent with respect to a dermatophyte in the subungual space. The treatment protocol typically includes a series of administrations, typically at least 4 weeks spaced apart, which achieves cure rates well above 70% after no more than 12 months of administration.

19 Claims, No Drawings

(56) References Cited

OTHER PUBLICATIONS

International Search Report and Written Opinion for International Application No. PCT/US20/54710 dated Feb. 11, 2021; 19 pgs.

Jublia (efinaconazole) topical solution, 10%, FDA Prescribing Information by Valeant Pharmaceuticals North America LLC, Bridgewater, New Jersey 08807; Issued Jun. 2014; 13 pgs.

Kathe et al., "Film forming systems for topical and transdermal drug delivery," Asian Journal of Pharmaceutical Sciences, 2017; 12:487-497.

Leeyaphan et al., "Dermatophytoma: An under-recognized condition," Indian J Dermatol Venereol Leprol., 2016; 82:188-9. Retrieved from http://www.ijdvl.com/text.asp?2016/82/2/188/165539.

McAuley et al., "An investigation of how fungal infection influences drug penetration through onychomycosis patient's nail plates," European Journal of Pharmaceutics and Biopharmaceutics, 2016; 102:178-184.

Osborne et al., "Antifungal drug response in an in vitro model of dermatophyte nail infection," Medical Mycology, Apr. 2004; 42:159-163.

Pollak et al., "Efinaconazole Topical Solution, 10%: Factors Contributing to Onychomycosis Success," J. Fungi, 2015; 1:107-114.

Pollak et al., "The Impact of New Topical Antifungals on Onychomycosis Management," Oct. 2017; 30(10); 12 pgs. Retrieved from https://www.podiatrytoday.com/impact-new-topical-antifungals-onychomycosis-management.

Schafer-Korting et al., "Fungicidal Activity Plus Reservoir Effect Allow Short Treatment Courses with Terbinafine in Tinea pedis," Skin Pharmacol Physiol 2008; 21:203-210.

Seebacher, Claus, "Action mechanisms of modern antifungal agents and resulting problems in the management of onychomycosis," Mycoses, 2003; 46:506-510.

Vlahovic, Tracey C., "Differentiating Nail Diseases With Dermoscopy," Podiatry Today, Dec. 2018; 31(12):20-25.

Vlahovic, Tracey, "When a Patient Presents With Linear Streaks in a Nail," Podiatry Today, Nov. 2015; 28(12):20-24.

Zaias, Md et al., "The Successful Treatment of Trichophyton rubrum Nail Bed (Distal Subungual) Onychomycosis With Intermittent Pulse-Dosed Terbinafine," Arch Dermatol., 2004; 140:691-695.

Elewski et al, "Access of Efinaconazole Topical Solution, 10%, to the infection Site by Spreading Through the Subungual Space" Journal of Drugs in Dermatology, 2014, vol. 13, Issue 11 pp. 1394-1398.

EPO, EESR dated Sep. 12, 2023, pp. 1-9.

JPO First Office Action dated Sep. 8, 2023, pp. 1-5.

* cited by examiner

ONYCHOMYCOSIS TREATMENT METHODS

This application claims priority to our U.S. provisional application with the Ser. No. 63/171,457, filed Apr. 6, 2021, and further claims priority to our U.S. application with the Ser. No. 17/474,656, filed, Sep. 14, 2021, which claims priority to commonly owned PCT Patent Application No. with the serial number PCT/US2020/054710, filed Oct. 8, 2020, which claims priority to U.S. provisional application with the Ser. No. 62/912,494, filed Oct. 8, 2019, all of which are incorporated by reference herein.

FIELD OF THE INVENTION

The field of the invention is compositions and methods for treatment of the subungual space, especially as it relates to treatment of onychomycosis and/or dermatophytoma.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Onychomycosis is a fairly common infection of the nail bed. Due to the location of the infection, delivery of sufficiently high (therapeutically effective) concentrations of antifungal agents has been difficult. Moreover, as a fungal infections typically include dividing cells as well as spores, therapeutically effective concentrations are relatively high even for highly potent agents as fungal spores are significantly less sensitive to antifungal agents. For example, terbinafine is a potent antifungal agent, approved for treatment of onychomycosis in oral form. While the oral form has been somewhat effective in treatment of the disease due to systemic delivery of drug to the soft tissue under the nail (nail bed) where the disease-causing dermatophytes proliferate, treatment success is often limited due to the systemic (especially hepatic) toxicity of terbinafine. Indeed, monotherapy was shown to be associated with a high rate of failure due to the low local drug concentration at the nail bed and the need for a high minimum inhibitory concentration (MIC) in the nail bed and nail plate (see e.g., *Mycoses* 2003, 46, 506-510).

To mitigate problems associated with toxicity, intermittent pulsed doses of 250 mg/day for 7 days every 2-4 months have been implemented with at least some improvement in outcome (see e.g., *Arch Dermatol* Vol 140, June 2004, p 691-695). However, the cure rates were still less than desirable and potential toxicity risks remained. Local administration of higher drug concentrations have been attempted with the hope to avoid hepatotoxicity and to achieve higher local drug concentrations. For example, antifungal drugs were topically applied to the nail plate as an alcoholic solution of 10% efinaconazole (marketed as JUBLIA™). Unfortunately, fairly low penetration of the nail plate led to only modest complete cure rates between 15.2% and 17.8% of treated population (see FDA Prescribing Information).

More recently, subungual administration had been proposed as a means to deliver antifungal agents to the site of infection, and exemplary compositions and methods are described in US 2013/0210925. Similarly, US 2010/0048724 and U.S. Pat. No. 9,446,009 teach non-liquid terbinafine HCl salt compositions for direct administration to the subungual space, and U.S. Pat. No. 7,135,194 teaches solid or semi-solid formulations for subungual administration. In still further example, semi-solids were used for subungual delivery as described in US 2004/0062733 and US 2007/0014743. However, while moderately high drug concentrations were at least locally administered, delivery of terbinafine from the solid or semi-solid carrier often fails to facilitate diffusion of the active agent to adjacent areas and as such once more led to less than desirable cure rates. Moreover, such solid or semi-solid carriers also often will not promote diffusion of the active agent into the nail bed and nail plate. Therefore, the carrier typically needed to be inserted into the leading edge of the diseased area which led in many cases to trauma and punctile bleed, resulting in lifting of the nail plate.

Still further compounding the difficulties with known subungual administration is the presence of a polysaccharide matrix that is produced by the fungal mass, which presents itself as "dermatophytoma". Indeed, where such a polysaccharide matrix is extensive, decreased penetration of antifungal agents renders the condition often resistant to commonly known antifungal therapies, and surgical removal of the nail plate in combination with oral terbinafine is often the only available manner of treatment. Even with such drastic options, efficacy in curing onychomycosis is still limited.

Thus, even though various compositions and methods of treating onychomycosis are known in the art, all or almost all of them suffer from several drawbacks. More specifically, currently known compositions and methods fail to effectively cure onychomycosis and/or dermatophytoma and further fail to achieve sustained remission of fungal infection/disease. Therefore, there is still a need to provide improved treatment compositions and methods that achieve desirable cure rates for onychomycosis and even for dermatophytoma.

SUMMARY OF THE INVENTION

The inventive subject matter is directed to various compositions and methods of treatment for onychomycosis and/or dermatophytoma that achieve a high cure rate and sustained remission of the fungal infection/disease. Advantageously, the compositions used for the treatment methods presented herein enable minimum inhibitory concentrations of the antifungal agent beyond the subungual space into a larger treatment space (including the nail plate). In addition, the treatment methods presented herein allow for atraumatic administration and preserve existing nail structure while allowing new and healthy nail plate to replace old and diseased nail plate during outgrowth of the nail. The dermatophyte in some examples is *Trichophyton* spec.

In one aspect of the inventive subject matter, the inventors contemplate a method for treating onychomycosis using a treatment protocol to subungually administer an antifungal agent in a liquid pharmaceutical composition. A plurality of subungual administrations is aimed at achieving a cure rate of at least 70% after no more than 12 months of treatment.

Atraumatic administration of the pharmaceutical composition using a cannula with preferably a blunt tip is envisioned with various schedules of administration, for example the first one or two treatments being applied every 30 days or so, with subsequent treatments being applied once every two months for the remainder of the treatment. In other examples, a series of bi-weekly administrations may be followed by another series of bi-monthly administrations.

During at least some or each of the treatments, a blunt tip of the cannula is envisioned to be advanced through the hyponychium towards a disease margin without necessarily having to contact the disease margin. In other examples, the blunt tip cannula is advanced through a polysaccharide matrix produced by a fungal mass in the subungual space. In further examples, the tip of the cannula is advanced to a central area of the diseased area. Administration of the composition into one or a plurality of distinct locations under the same nail plate is also contemplated.

In another aspect of the inventive subject matter, a storage stable liquid pharmaceutical composition which comprises a pharmaceutically acceptable carrier and an antifungal drug dissolved therein is formulated with a viscosity that enables penetration of the composition through a polysaccharide matrix produced by a fungal mass in the subungual space. The viscosity of the manufactured composition is between 500 cP(mPa*s) and 2,500 cP(mPa*s). In other examples, the viscosity of the composition may be higher, up to 50,000 cP(mPa*s). The composition in this case may be slightly heated prior to administration into the subungual space (e.g., to a temperature not exceeding 60° C.) so as to temporarily reduce its viscosity and assure suitable flowing characteristics. Once delivered in place, the composition is allowed to cool down to body temperature or less, which restores a higher initial viscosity and reduces the risk of incidental leakage of the composition from the subungual space. Preferably, administration is performed in a hydrophobic vehicle to reduce high local dosage administration without any significant systemic adsorption of the active agent.

In yet further examples, the subungual administration of the composition comprises a plurality of distinct administrations at respective distinct locations under the same nail plate. As much as 150 μL may be administered into a subungual space at any given administration of the composition for a single nail, and in some cases the amount may be even higher due to a large subungual space and/or partial lifting of the nail plate. In other examples, administration of the pharmaceutical composition is performed in an amount of between 10 and 50 μL, or between 20 and 70 μL or 10 and 50 μL.

In preferred aspects, a storage-stable liquid pharmaceutical composition comprises a pharmaceutically acceptable carrier and an antifungal agent, for example, an allylamine antifungal drug such as terbinafine, dissolved in the pharmaceutically accepted carrier at a concentration of 10 wt %, 20 wt %, 30 wt %, 40 wt %, or more. The antifungal agent is selected with a suitable inhibitory concentration to exceed a minimal inhibitory concentration so as to provide an effective antifungal treatment. In some examples, each of the administered doses of the composition generates, at least in a subungual space, a minimum inhibitory concentration of the antifungal agent with respect to a dermatophyte in the same subungual space. The aim of the treatments is to deliver sufficient number of doses to eradicate substantially all of the dermatophyte in the subungual space. In further examples, each of the doses generates the minimum inhibitory concentration of the antifungal agent in a treatment space that extends beyond the subungual space, for example by at least 0.1 mm, or 0.2 mm, or 0.5 mm and even more. The plurality of doses of the composition are delivered on a predetermined schedule designed to substantially eradicate all of the dermatophyte in the subungual space, preferably within equal or less than 12 months.

The pharmaceutically acceptable carrier, in turn, preferably comprises a hydrophobic solvent and/or a viscosity control agent. The pharmaceutical composition is also characterized by a stable storage life, wherein no more than 5% total degradation products form from the antifungal agent after a storage period of at least one month at a temperature of 40° C. The hydrophobic solvent of the pharmaceutically acceptable carrier comprises in some embodiments at least one solvent selected from the group consisting of isostearic acid, benzyl alcohol, diisopropyl adipate, diethyl sebacate, and isopropyl myristate, and wherein an optional hydrophilic solvent is selected from the group consisting of dimethyl isosorbide, propylene carbonate, and D,L-lactic acid. Numerous alternative solvents and co-solvents are also contemplated herein.

Viscosity control agents of the composition of the method may include an acrylic polymer or a cellulose-based thickener, such as ethyl cellulose, a hydroxyethyl cellulose, or a hydroxypropyl cellulose. In other embodiments, the viscosity control agent is a liquid-based thickener, such as cetyl alcohol, stearyl alcohol, carnauba wax, or a stearic acid. Numerous other viscosity control agents are also contemplated for the present inventive subject matter.

Advantageously, contemplated methods provide for (1) high adherence and penetration into the polysaccharide matrix that is often associated with dermatophytoma and/or onychomycosis, (2) high local dose and duration of effective drug availability, and (3) high secondary diffusion in the nail plate and nail bed accompanied by low systemic adsorption of the therapeutic agent to minimize its systemic toxicity. Furthermore, these compositions are stable during storage and may be clinically administered employing a method that does not induce pain and/or trauma.

Various objects, features, aspects, and advantages of the inventive subject matter will become more apparent from the following detailed description of preferred embodiments.

DETAILED DESCRIPTION

The inventors have now discovered methods for subungual administration of a liquid pharmaceutical composition that allow for a high topical concentration of an antifungal agent in a pharmaceutically acceptable carrier, which enables sustained concentrations of the antifungal agents well above the minimum inhibitory concentration (MIC) of the antifungal agent in the treatment space. Consequently, therapeutically effective antifungal activity will be sustained in the treatment space over extended periods of time and so lead to significantly improved cure rates of onychomycosis and even dermatophytoma.

Contemplated carriers preferably comprise one or more hydrophobic solvents and an optional hydrophilic solvent. The pharmaceutical composition is formulated to have a viscosity that not only allows for targeted delivery thereof to the subungual space via a small-bore cannula, but also allows for lateral, proximal, and distal passive distribution of the liquid pharmaceutical composition through the subungual space, typically via translation, capillary action, and/or surface tension. Advantageously, the compositions presented herein will also allow for diffusion of the antifungal agent into the nail plate at concentrations at or above the MIC while largely avoiding systemic absorption into the circulatory system of a patient and binding of the active agent to the keratin. Moreover, the compositions presented herein enable the distribution of the pharmaceutical composition into and through the polysaccharide matrix of a dermatophytoma, and consequently are also suitable for treatment of both onychomycosis and dermatophytoma.

As used herein, the term "subungual space" refers to a pre-existing void space that is present between the nail bed and the nail plate, and that is a result of fungal growth in people with onychomycosis. Viewed from a different perspective, the subungual space may be considered a contiguous open space that may be empty, or that may include debris from keratin, collagen, and/or fungal material (such as a polysaccharide matrix). Therefore, the subungual space is typically a space of variable geometry that may extend over a significant portion of the nail organ, and that may further include areas that are co-extant with current and/or prior fungal growth. Thus, from a drug administration perspective, the subungual space is a space that is accessible from a location outside the nail organ without damage to or separation of the nail plate and nail bed upon access. For example, administration of a composition as contemplated herein can be performed with a small gauge blunt-tip cannula without producing a punctile bleed and nail plate/nail bed separation.

The term "subungual space" is therefore distinct from the term "treatment space" in that the treatment space will also include areas that are outside the subungual space but in which the active ingredient will be present (e.g., via diffusion), preferably in an amount that is at least the MIC (minimum inhibitory concentration) of the active agent as is discussed in more detail below. Consequently, the treatment space in most cases will be more extensive than the subungual space and will include an area that has not directly contacted a treatment composition upon administration. For example, the treatment space will typically include a space within which the active ingredient is present due to diffusion and/or nail growth. For example, where a highly concentrated terbinafine solution was atraumatically administered into the subungual space, the treatment space includes space adjacent to the subungual space in which the terbinafine is present in at least MIC and a portion of the nail plate into which the terbinafine has diffused. Notably, such region in the nail plate may continually expand the treatment space as the nail grows distally.

With regard to the term "liquid" as used in conjunction with compositions contemplated herein, it is noted that the term liquid refers to compositions that comprise a liquid component (typically a solvent that is liquid at room temperature) that may have one or more other components (e.g., antifungal agent) dissolved, dispersed, or otherwise distributed therein. Additionally, a solid may be de-stabilized into an amorphous phase, which may appear as a liquid. Consequently, the terms "liquid" compositions and "flowable" compositions are used interchangeably herein. Most typically, liquids contemplated herein will have a dynamic viscosity of between 500 and 2,500 cP(mPa*s). In other embodiments, the liquid of the present composition will have a dynamic viscosity of between 750-1,500 cP (mPa*s).

Consequently, it should be appreciated that contemplated compositions and methods allow for therapeutic coverage of the entire mycotic nail bed, eradicating the proliferating and non-proliferating spores quickly so that new disease-free nail plate and nail bed below can replace the mycotic tissue (concurrent with linear growth). Due to the relatively high concentration of active agent (such as terbinafine), an antifungal agent-filled reservoir is created that can spread from the site of deposition proximally through the ridges and caverns of the nail bed. Moreover, due to the hydrophobic nature of the carrier, the active agent is quickly absorbed into the nail plate and so forms an antifungal barrier that may prevent subsequent proximal and ventral fungal invasion. It should also be recognized that the hydrophobic nature of the carrier will reduce systemic absorption of the active agent, while at the same time partitioning of the active agent into the nail plate is promoted. In addition, contemplated formulations have a viscosity that balances fluid distribution in the subungual space with the ability to deliver the formulation through small-bore cannulas (e.g., blunt-tip 30-gauge cannula) to so prevent or significantly reduce further lifting of the nail plate (onycholysis). Moreover, the flowing nature of the compositions presented herein will also enable passive movement throughout the subungual space due to pressure waves encountered in the nail bed as a foot and toes cycle trough a normal gait.

It should be appreciated that such cannulas are sufficiently blunt to allow delivery of the active agent into the center of the mycotic nail bed space without trauma or damage to the nail bed epithelium, and precise enough to allow a physician to treat entry points such as the lateral edge, and even the center of a difficult-to-treat fungal mass (dermatophytoma). Viewed from a different perspective, proper viscosity and administration of contemplated formulations will balance numerous requirements for a therapeutic effect: Retention of a liquid composition in the subungual space at therapeutic quantities, while allowing for atraumatic administration and passive distribution (e.g., via capillary action and/or mechanical force due to toe movement) of the liquid formulation throughout the subungual space without significant loss due to leakage. Most preferably, such administration is performed using a blunt cannula having a size that prevents trauma. The delivery cannula may be straight or may have a bent tip. The cannula may be metal or plastic, with the possible advantage of the plastic cannula in its ability to atraumatically penetrate deeper into the subungual space due to its natural flexibility.

The subungual space under the nail plate may be prepared for delivery of the pharmaceutical composition of the inventive subject matter, for example, by injecting of (pressurized) dry air prior to administration of the composition. Such preparatory step may help to open up the cavernous voids of the subungual space and remove loose debris therefrom so as to ease subsequent delivery of the pharmaceutical composition and maximize its filling volume following such preparatory step.

Terbinafine (or other suitable antifungal drug) liquid formulations for treatment of onychomycosis are directed towards flowable liquid forms of terbinafine that can be delivered topically under the nail plate with very high local drug concentrations, and where desired also onto the surface of the nail bed and/or hyponychium. The concentrated and viscous liquid formulation is preferably delivered through a small-bore cannula using a suitably sized manually activated or motor driven syringe.

While not limiting to the inventive subject matter, it is generally preferred that the step of subungual administration of the liquid pharmaceutical composition comprises a step of atraumatically inserting a cannula between the nail plate and the nail bed and another step of administering the liquid pharmaceutical composition through the cannula. Preferably, but not necessarily, the cannula is a blunt-tip cannula having at least one lateral opening in a distal portion of the cannula. Alternatively, blunt tip cannulas may also have a distal opening. Moreover, it is noted that the subungual space will typically include an area infected with a fungus where the nail plate has partially detached from the nail bed (onycholysis). However, it should be noted that the liquid pharmaceutical composition need not be directly delivered to the infected area, but that the liquid pharmaceutical composition may passively migrate to the infected area by action of both translation and diffusion. Advantageously, the step of administering the liquid pharmaceutical composition into the subungual space also ascertains the minimum therapeutic concentration of the therapeutic agent in the nail bed and nail plate. In further advantageous aspects, it should be recognized that the compositions contemplated herein will have the antifungal agent at concentrations well exceeding the MIC to so provide a longer period of antifungal protections, and in some cases be even toxic to dormant spores.

It is further contemplated that the treatment is designed to achieve at least a MIC (minimum inhibitory concentration) of the active agent after every delivery of the composition into the subungual space. In various examples of the inventive subject matter, the concentration of the active agent after delivery is above the MIC, for example by a factor of at least two times higher, or at least 3 times higher, or at least four times higher, or at least 5 times higher, or at least 6 times higher, or at least seven times higher, or at least 8 times higher, or at least nine times higher, or at least ten times higher, or at least twenty times higher, or at least fifty times higher, or at least one hundred times higher than MIC for a particular fungus affecting the nail bed. Likewise, the administered composition will have a sufficiently high concentration of the antifungal agent to so ensure a duration of a MIC in the subungual space and at least portions of the treatment space for at least 1 day, and more preferably at least 3 days, or at least 7 days, or at least 2 weeks, or at least three weeks, or at least one month, or at least 2 months.

Viewed from a different perspective, it is contemplated that the administered composition will have a sufficiently high concentration of the antifungal agent to so ensure an MIC of the antifungal agent in the distally growing nail plate. Consequently, it should be recognized that antifungal agent will be detectable in nail clippings about 1 month, or about 2 months, or about 3 months, or about 4 months, or about 6 months, or about 8 months after initial administration (which is typically followed by subsequent administrations in 1- and/or 2-month intervals). Most typically, the antifungal agent will be detectable in nail clippings at a concentration of at least 70%, or at least 80%, or at least 90%, or at least 100%, or at least 120%, or at least 140% of the MIC for the particular antifungal agent and dermatophyte.

During the time period after the administration of the pharmaceutical composition, the concentration of the active agent may diminish over time. Accordingly, contemplated methods will assure that at least a MIC level is maintained at all times throughout the treatment period. In some examples, the level of the active antifungal agent in the subungual space and/or in the treatment space is not allowed to drop below at least two times higher, or at least 3 times higher, or at least four times higher, or at least 5 times higher, or at least 6 times higher, or at least seven times higher, or at least 8 times higher, or at least nine times higher, or at least ten times higher than MIC for a particular fungus affecting the mail bed at any time during the treatment period so as to maintain high potency of the antifungal agent and preserve high efficacy of the treatment.

Determination of the MIC can be done from time to time, such as prior to subsequent administration so as to control proper administration and verify ongoing effectiveness of the treatment. Such determination of the MIC level can done by analyzing the treatment area and the nail plate, for example by analyzing nail clippings, nail scrapings, or another sample retrieved from the treatment area. Alternatively, visual inspection to detect fungus and/or reduction in diseased area may serve as a manner of verification of MIC.

The data below show experimental determination of MIC and the minimum fungicidal concentrations (MFC) levels for a variety of commonly encountered fungi as examples of minimal levels of concentrations achieved using the methods of the present inventive subject matter.

TABLE 1

MIC and MFC values in the presence and absence of keratin for 25% composition in surfactant against the *T. mentagrophytes* strains tested (μg/mL).

| | | 25% composition in surfactant | | | |
|---|---|---|---|---|---|
| Organism | MRL # | MIC | MFC | MFC with Keratin | Change in MFC (dilutions) |
| *T. mentagrophytes* | 40687 | 0.004 | 4 | 4 | 0 |
| *T. mentagrophytes* | 40931 | 0.004 | 2 | 4 | +1 |
| *T. mentagrophytes* | 41033 | 0.002 | 1 | 4 | +2 |
| *T. mentagrophytes* | 41037 | 0.002 | 8 | 8 | 0 |
| *T. mentagrophytes* | 41182 | 0.002 | 2 | 4 | +1 |
| *T. mentagrophytes** | 24426 | 0.001 | 2 | 4 | +1 |
| *T. mentagrophytes** | 24887 | 0.002 | 4 | 4 | 0 |

*Amorolfine-resistant strains

TABLE 2

MIC and MFC values in the presence and absence of keratin for 25% composition 25 w/w % in surfactant against the *T. rubrum* strains tested (μg/mL).

| | | 25% composition in surfactant | | | |
|---|---|---|---|---|---|
| Organism | MRL # | MIC | MFC | MFC with Keratin | Change in MFC (dilutions) |
| *T. rubrum* | 42055 | 0.002 | 0.25 | 4 | +4 |
| *T. rubrum* | 42106 | 0.008 | 0.125 | 0.125 | 0 |
| *T. rubrum* | 42232 | 0.016 | 1 | 0.5 | −1 |
| *T. rubrum* | 42233 | 0.004 | 0.03 | 4 | +7 |
| *T. rubrum** | 31517 | 0.002 | >64 | 64 | −1 |
| *T. rubrum** | 31925 | 0.002 | 2 | 8 | +2 |

*Amorolfine-resistant strains

TABLE 3

MIC and MFC values in the presence and absence of keratin for terbinafine hydrochloride against the *T. mentagrophytes* strains tested (μg/mL).

| | | Terbinafine | | | |
|---|---|---|---|---|---|
| Organism | MRL # | MIC | MFC | MFC with Keratin | Change in MFC (dilutions) |
| *T. mentagrophytes* | 40687 | 0.008 | 0.5 | 16 | +5 |
| *T. mentagrophytes* | 40931 | 0.008 | 2 | 4 | +1 |
| *T. mentagrophytes* | 41033 | 0.008 | 0.125 | 4 | +5 |
| *T. mentagrophytes* | 41037 | 0.008 | 8 | 16 | +1 |
| *T. mentagrophytes* | 41182 | 0.008 | 4 | 4 | 0 |
| *T. mentagrophytes** | 24426 | 0.008 | 4 | 4 | 0 |
| *T. mentagrophytes** | 24887 | 0.016 | 2 | 4 | +1 |

*Amorolfine-resistant strains

TABLE 4

MIC and MFC values in the presence and absence
of keratin for terbinafine hydrochloride against
the *T. rubrum* strains tested (μg/mL).

| | | Terbinafine | | | |
|---|---|---|---|---|---|
| Organism | MRL # | MIC | MFC | MFC with Keratin | Change in MFC (dilutions) |
| *T. rubrum* | 42055 | 0.004 | 0.25 | 0.125 | −1 |
| *T. rubrum* | 42106 | 0.016 | 0.5 | 2 | +2 |
| *T. rubrum* | 42232 | 0.016 | 1 | 1 | 0 |
| *T. rubrum* | 42233 | 0.008 | 0.125 | 4 | +5 |
| *T. rubrum** | 31517 | 0.004 | 0.125 | 0.125 | 0 |
| *T. rubrum** | 31925 | 0.004 | 2 | 4 | +1 |

*Amorolfine-resistant strains

In still another aspect of the inventive subject matter, the inventors contemplate a method of treating onychomycosis that includes a step of subungually administering a liquid pharmaceutical composition through a cannula inserted to location that does not need to contact a visible proximal edge of an area affected by onychomycosis, and where the liquid composition migrates to a visible proximal edge of an area affected by onychomycosis. Viewed from yet another perspective, the inventors contemplate a method of delivering and retaining a liquid pharmaceutical composition comprising an antifungal agent in a subungual treatment space that includes a step of subungually administering the liquid pharmaceutical composition into the subungual space. Therefore, the proximal end of the cannula may be at least 0.5 mm, or at least 0.7 mm, or at least 0.9 mm, or at least 1.1 mm, or at least 1.3 mm, or at least 1.5 mm, or at least 1.7 mm, or at least 1.9 mm, or at least 2 mm away from the visible proximal edge of the area affected by onychomycosis. The antifungal composition may then migrate by diffusion and/or translation (typically via compressive forces) to the affected area.

Significantly, the local delivery and retention of the active antifungal agent to the disease location is not dependent on systemic absorption of the drug. Indeed, the use of a hydrophobic solvent helps prevent partitioning of the active antifungal agent (preferably terbinafine) into the capillary system of the nail bed. Thus, very high local drug concentrations can be achieved with the topical subungual administration method without the risk of liver toxicity associated with the systemic oral drug administration. The increased therapeutic effect is thought to be produced by the high concentration of the antifungal agent (e.g., terbinafine), the motility and retention of the antifungal agent (e.g., terbinafine) in the subungual space at high concentrations, and the diffusion of the antifungal agent (e.g., terbinafine) from the hydrophobic solvent into the nail plate to achieve therapeutically effective concentrations in the nail plate. As the nail plate advances distally during nail growth, the antifungal agent (e.g., terbinafine) diffused and retained in the nail plate will present an effective barrier to fungal growth and re-establishment, and a healthy nail plate will ultimately have replaced diseased nail plate via growth. Such barrier effect will be further augmented by subsequent administrations(s) of the formulations contemplated herein to the subungual and treatment space. As will be readily appreciated, subsequent administrations will typically require a reduced volume of the therapeutic composition as new and healthy nail bed and nail plate replace the affected subungual space due to distal growth.

In view of the above, it should therefore be recognized that contemplated uses especially include various methods of subungual administration in a mammal. In such methods, it is typically contemplated that the liquid pharmaceutical compositions presented herein are subungually administered to a space that is located between the nail plate and the nail bed, typically via direct administration from a cannula that is inserted through or beyond the hyponychium into the subungual space. In this context, it should also be recognized that the administration of the liquid pharmaceutical composition does not require initial direct contact with the affected zone or border of infection as the liquid composition is flowable and can passively move to the affected zone (e.g., by compression and pressure relief during ordinary daily activity). Moreover, it should be noted that the subungual administration can be performed at various positions along the hyponychium and the number of distinct administration sites will at least in part be determined by the extent and location of the fungal growth and damage to the nail bed and nail pate.

Typically, administration through a cannula will require insertion of the cannula through the hyponychium and advancement of the cannula into the subungual space between the nail plate and the nail bed. Most preferably, the cannula is a blunt-tip cannula (e.g., 25-gauge, 26-gauge, 28-gauge, 30-gauge) with one or two lateral openings in a distal portion of the cannula. Moreover, it is also preferred that the liquid pharmaceutical composition is administered to fill at least 50%, or at least 60%, or at least 70%, or at least 80%, or at least 90%, or at least 95% of the void space between the nail bed and the nail plate. Where desired, administration may also include topical administration in the lateral nail fold. Administration may also be performed in the open space between the nail bed and nail plate where fungal presence is abundant.

Administration of the composition of the inventive subject matter, is performed more than once and on a predetermined schedule. A plurality of subungually delivered administrations is aimed at achieving a cure rate of at least 70% after no more than 12 months of treatment. In other examples, at least 80%, or at least 90%, or at least 95% of cure rate is achieved following twelve months of treatment. In further examples, at least 70% cure rate, or at least 80% cure rate, or at least 90% of cure rate is achieved after no more than 10 months of treatment. In further yet examples, at least 70% cure rate, or at least 80% cure rate, or at least 90% of cure rate is achieved after no more than 8 months of treatment.

The term "cure rate" is generally used herein to define a state of a lack of the onychomycosis or any other related nail fungal disease. It may be detected using one or more of the following observations and methods:

a. lack of visible distortion to the nail appearance, or, in other words, similarity between the appearance of the affected nail and other healthy nails:

b. lack of pain near the nail plate:

c. lack of odor coming from the nail:

d. lack of nail brittleness:

e. restoration of regular nail thickness:

f. lack of recurrence of visible onychomycosis after at least 1 week, or after at least 2 weeks, or after at least 3 weeks, or after at least 1 month, or after at least 3 months, or after at least 6 months, or after at least 12 months, or even longer:

g. lack, or presence below an acceptably low threshold of detectable fungal cells or spores in nail clippings, scraping or in a sample recovered from subungual space, as confirmed using microscopic evaluation, a laboratory test, a molecular test, a microbiological test, or other suitable tests to detect a presence or absence of fungal cells or spores.

Atraumatic administration of the pharmaceutical composition using a cannula with preferably a blunt tip is envisioned with various schedules of administration. A predetermined schedule of treatments defines one or more frequencies of treatments, the total number of treatments and the details of each treatment. In some examples, the first one, two, three, four, or five treatments are applied every 30 days (±5 days), with subsequent treatments being applied once every two months (±1 week) for the remainder of the treatment period. The overall treatment period takes at least 4 months, at least 6 months, at least 8 months, at least 10 months, at least 12 months, at least 14 months, at least 16 months, at least 18 months, or even longer. The total number of composition administrations is at least 2, at least 3, at least 4, at least 6, at least 8, at least 10, at least 12, at least 14, at least 16, at least 18 applications, or even more. In other examples, a series of bi-weekly administrations over a period of at least 1 months, at least 2 months, at least 3 months, at least 4 months, or even longer may be followed by another series of bi-monthly administrations over an additional period of at least 2 months, at least 4 months, at least 6 months, at least 8 months, at least 10 months, at least 12 months, at least 14 months, at least 16 months, at least 18 months, or even longer.

Individual applications of the composition may be the same or different throughout the treatment period. In one example, multiple administrations to the center and peripheral areas of the subungual area during the single treatment may be performed during the initial 1, 2, 3, 4, 5, 6, 7, 8, 9, 10 administration or more, which is followed by only a single administration to the central area of the disease margin during each treatment the remainder of the treatments. In other example, multiple administrations may alternate with single administrations. The overall volume of administered composition may be the same or different throughout the treatment period.

In some examples, a consistent volume of composition is administered during every treatment, while in other examples, a larger volume of composition may be administered initially, following by gradually diminishing volume of the composition applied during the latter part of the treatment period. In some examples, the subungual administration of the composition comprises a plurality of distinct administrations at respective distinct locations under the same nail plate. As much as 100 µL is delivered at any given single administration of the composition. In other examples, administration of the pharmaceutical composition is performed in an amount of between 10 and 50 µL, or 20 and 75 µL, which is given in 1, 2, 3, 4, 5, 6, 7, 8, 9, or 10 administrations during a single treatment session.

During at least some or each of the treatments, a blunt tip of the cannula is envisioned to be advanced through the hyponychium towards a disease margin without contacting the disease margin. In other examples, the blunt tip cannula is advanced through a polysaccharide matrix produced by a fungal mass in the subungual space. In further examples, the tip of the cannula equipped with one or more central or lateral openings is advanced to a central area of the diseased area. Administration of the composition into one or a plurality of distinct locations under the same nail plate is also contemplated using one or more intermittent or continuous administrations.

In another aspect of the inventive subject matter, a storage stable liquid pharmaceutical composition which comprises a pharmaceutically acceptable carrier and an antifungal drug dissolved therein is formulated with a viscosity that enables penetration of the composition through a polysaccharide matrix produced by a fungal mass in the subungual space. The viscosity of the manufactured composition is between 500 cP(mPa*s) and 2,500 cP(mPa*s), or between 750 cP(mPa*s) and 1,500 cP(mPa*s).

In other examples, the viscosity of the composition may be higher, up to 50,000 cP(mPa*s). The composition in this case may be manufactured as a gel at room temperature. Dynamic viscosity of the composition is between 2,500 and 10,000 cP (mPa*s), or no more than 20,000 cP (mPa*s), or no more than 30,000 cP (mPa*s), or no more than 40,000 cP (mPa*s), or no more than 50,000 cP (mPa*s). The composition may be slightly heated prior to delivery into the subungual space to a temperature not exceeding 40° C., or 45° C., or 50° C., or 55° C., or 60° C. so as to temporarily reduce its viscosity and assure suitable liquid-like flowing characteristics. Once delivered in place, the composition is naturally cooled down to the body temperature or less, which restores a higher initial viscosity and reduces its flowing tendency, whereby reducing a risk of accidental leakage of the composition from the subungual space.

A storage-stable liquid pharmaceutical composition comprises a pharmaceutically acceptable carrier and an antifungal agent, for example, an allylamine antifungal drug such as terbinafine, dissolved in the pharmaceutically accepted carrier at a concentration of 10 wt %. 15 wt %, 20 wt %, 30 wt %, 40 wt % (e.g., 42 wt %), or more. The antifungal agent is selected with a suitable inhibitory concentration to exceed a minimal inhibitory concentration so as to provide an effective antifungal treatment. In some examples, each of the administered doses of the composition generates, at least in a subungual space, a minimum inhibitory concentration of the antifungal agent with respect to a dermatophyte in the same subungual space. The aim of the treatments is to deliver sufficient number of doses to eradicate substantially all of the dermatophyte in the subungual space. In further examples, each of the doses generates the minimum inhibitory concentration of the antifungal agent in a treatment space that extends beyond the subungual space, for example by at least 0.5 mm, or at least 1.0 mm, or at least 2.0 mm, or more. The plurality of doses of the composition are delivered on a predetermined schedule designed to substantially eradicate all of the dermatophyte in the subungual space within equal or less than 12 months of treatment.

Terbinafine is most commonly provided as a hydrochloride salt, which appears as a crystalline high melting solid. A free-base form of terbinafine is also known, appearing as a lower melting crystalline solid. Liquid forms of terbinafine may be prepared by dissolving the solids in solvents. However, concentrations that can be achieved are limited by solubility, as well as the pharmaceutical acceptability of the solvent used. More useful in achieving high drug concentration is an amorphous form of terbinafine that appears as a liquid at room temperature. An amorphous form of terbinafine may be therefore be prepared by identifying an appropriate crystallization inhibitor designed to prevent formation of the thermodynamically preferred crystalline solid. However, the lower melting free base form is more amenable to stabilizing the substance in the liquid state, and further benefits from the absence of material weight associated with the counter ion that occurs with a salt form.

In some examples, a storage stable liquid pharmaceutical composition of the inventive subject matter comprises a pharmaceutically acceptable carrier and an antifungal drug dissolved therein at a concentration of at least 10 wt %. in further examples, the antifungal drug is dissolved at a concentration of at least 15 wt %, at least 20 wt %, at least 30 wt %, or at least 40 wt %. The antifungal drug remains, after storage at a temperature of 40° C. for at least one month, dissolved or dispersed in the carrier that allows subungual administration of the composition through a cannula without clogging the cannula.

Most notably, it should therefore be recognized that the combination of hydrophobic solvent(s) and polymeric film forming agent will facilitate during and after administration to the subungual space lateral, proximal, and distal mobility within the subungual space while retaining the liquid pharmaceutical composition within the subungual space. Moreover, due to the specific composition, the liquid pharmaceutical composition will also penetrate into and through the polysaccharide matrix that is often associated with the fungal infection. Therefore, administration of the contemplated formulations need not necessarily be up to the leading edge of the diseased area but may be to a location that is somewhat removed from the edge (e.g., at least 0.5 mm away, or at least 1 mm away, or at least 2 mm away, or at least 3 mm away, or at least 5 mm away).

EXAMPLES

The following examples are provided to illustrate various aspects of the inventive subject matter and are not intended to limit the inventive subject matter.

Representative compositions: Table 5 provides exemplary containing terbinafine as the antifungal agent and having a viscosity of approximately between 750-1,500 cP (mPa*s). The compositions can be used for subungual administration using a prefilled syringe and a 28 gauge blunt tip cannula.

TABLE 5

Storage stable antifungal compositions for subungual administration

| Component | Function | Wt % Composition | | | |
| | | 1 | 2 | 3 | 4 |
| --- | --- | --- | --- | --- | --- |
| Terbinafine free base | Active ingredient | 42.00 | 42.00 | 42.00 | 42.00 |
| Butylated hydroxytoluene | Anti-oxidant | 0.20 | 0.20 | 0.20 | 0.20 |
| Benzyl alcohol | Solvent | 2.70 | 2.70 | | |
| Benzyl benzoate | Solvent | | | | |
| Diisopropyl adipate | Co-solvent | 20.00 | 20.00 | | |
| Diethyl sebacate | Co-solvent | | | | |
| Isopropyl myristate | Co-solvent | 31.10 | 32.10 | 5.80 | 7.80 |
| Isostearic acid | Solvent, Diluent | | | 25.00 | 22.00 |
| Isostearyl alcohol | Diluent | | | | |
| Dimethyl isosorbide | Solvent | | | 15.00 | 15.00 |
| Propylene carbonate | Solvent | | | 5.00 | 5.00 |
| D,L-Lactic acid | Solvent | | | 7.00 | 7.00 |
| Ethanol | Gelling vehicle, solvent | | | | |
| Hydroxypropyl cellulose | Gel agent, viscosity increase, film former | | | | |
| Ethyl cellulose | Gel agent, viscosity increase, film former | 4.00 | 3.00 | | 1.00 |

Exemplary administration: After thorough cleaning of the affected toe, a blunt tip annual was inserted through the hyponychium into a subungual space that was created by fungal growth. The proximal tip of the cannula did not contact the visible leading edge of the fungal growth, and the average insertion depth was approximately 2 mm. None of the probands reported pain, no bleeding occurred, and no treatment site reactions were observed. Administration volume varied between about 6.5 µl and 105 µl per nail, which was largely determined by the accessible volume of the subungual space. Therefore, the total administered dose was between about 2.5 mg and about 44 mg per nail. Cumulative dose administered per proband was between about 63 mg and 73 mg. All probands will report back within 1 month for the next administration. Anticipated administration schedule is at week 4, 8, 12, 20, 28, 36, and 44 with a final visit for evaluation at week 48 and 52 post initial administration.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

As used herein, the term "administering" a pharmaceutical composition or drug refers to both direct and indirect administration of the pharmaceutical composition or drug, wherein direct administration of the pharmaceutical composition or drug is typically performed by a health care professional (e.g., physician, nurse, etc.), and wherein indirect administration includes a step of providing or making available the pharmaceutical composition or drug to the health care professional for direct administration (e.g., via injection, infusion, oral delivery, topical delivery, etc.). It should further be noted that the terms "prognosing" or "predicting" a condition, a susceptibility for development of a disease, or a response to an intended treatment is meant to cover the act of predicting or the prediction (but not treatment or diagnosis of) the condition, susceptibility and/or response, including the rate of progression, improvement, and/or duration of the condition in a subject.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow; the meaning of "a." "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps ay be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A method of treating onychomycosis, comprising:
using a treatment protocol to subungually and atraumatically administer an antifungal agent in a liquid pharmaceutical composition;
wherein each administration generates at least in a subungual space a minimum inhibitory concentration of the antifungal agent with respect to a dermatophyte in the subungual space;
wherein the subungual space is a pre-existing void space between a nail bed and a nail plate that is accessible from a location outside a nail organ without damage to or separation of the nail plate and the nail bed;
wherein the treatment protocol comprises a plurality of subungual administrations that achieves a cure rate of at least 70% after no more than 12 months; and
wherein the pharmaceutical composition has a viscosity that enables penetration of the pharmaceutical composition through a polysaccharide matrix produced by a fungal mass in the subungual space.

2. The method of claim 1, wherein the cure rate is at least 80% after no more than 12 months, or wherein the cure rate is at least 70% after no more than 10 months.

3. The method of claim 1, wherein the treatment protocol comprises initial administration of the pharmaceutical composition every 30 days for the first two to four treatments, followed by a plurality of subsequent bi-monthly treatments.

4. The method of claim 3, wherein the plurality of subsequent bi-monthly treatments is at least three subsequent treatments.

5. The method of claim 1, wherein administration is performed using a blunt tip cannula that is advanced through the hyponychium towards a disease margin without contacting the disease margin, and optionally wherein the blunt tip cannula is advanced through a polysaccharide matrix produced by a fungal mass in the subungual space.

6. The method of claim 1, wherein the subungual administration comprises a plurality of distinct administrations at respective distinct locations under the same nail plate.

7. The method of claim 1, wherein each administration comprises administration of the pharmaceutical composition in an amount of equal or less than 150 µL.

8. The method of claim 1, wherein a majority of the plurality of subungual administrations comprises administration of the pharmaceutical composition in an amount of between 20 and 100 µL.

9. The method of claim 1, wherein the liquid pharmaceutical composition comprises a hydrophobic vehicle and is formulated to prevent systemic adsorption of the active agent.

10. The method of claim 9, wherein the antifungal agent is present in the liquid pharmaceutical composition at a concentration of at least 40 wt %.

11. The method of claim 10, wherein the pharmaceutical composition has a viscosity of between about 500-2,500 cP (mPa*s).

12. The method of claim 11, wherein the antifungal agent is an allylamine antifungal drug.

13. The method of claim 12, wherein the allylamine antifungal drug is terbinafine free base or a pharmaceutically acceptable salt of terbinafine.

14. A method of treating onychomycosis, comprising:
subungually and sequentially administering a plurality of doses of an antifungal agent in a liquid pharmaceutical composition;
wherein each of the doses generates at least in a subungual space a minimum inhibitory concentration of the antifungal agent with respect to a dermatophyte in the subungual space;
wherein the subungual space is a pre-existing void space between a nail bed and a nail plate that is accessible from a location outside a nail organ without damage to or separation of the nail plate and the nail bed;
wherein the plurality of doses eradicate at least 90% of the dermatophyte in the subungual space; and
wherein the pharmaceutical composition has a viscosity that enables penetration of the pharmaceutical composition through a polysaccharide matrix produced by a fungal mass in the subungual space.

15. The method of claim 14, wherein each of the doses generates the minimum inhibitory concentration of the antifungal agent in a treatment space that extends beyond the subungual space.

16. The method of claim 14, wherein the plurality of doses eradicates at least 90% of the dermatophyte in the subungual space within equal or less than 12 months.

17. A method of treating onychomycosis, comprising:
subungually administering multiple doses of an antifungal agent in a liquid pharmaceutical composition to a subungual space, wherein the antifungal agent in the pharmaceutical composition has a concentration of at least 20 wt %;
wherein the subungual space is a pre-existing void space between a nail bed and a nail plate that is accessible from a location outside a nail organ without damage to or separation of the nail plate and the nail bed;
wherein the antifungal agent has a concentration in the pharmaceutical composition that extends fungicidal action of the antifungal agent into a treatment space that extends beyond the subungual space; and
wherein the pharmaceutical composition has a viscosity that enables penetration of the pharmaceutical composition through a polysaccharide matrix produced by a fungal mass in the subungual space.

18. The method of claim 17, wherein the subungual space includes a polysaccharide matrix produced by a fungal mass in the subungual space.

19. The method of claim 17, wherein the treatment space extends at least in one direction at least 1.0 mm beyond the subungual space.

* * * * *